US00PP09141P

United States Patent [19]

Enthoven

[11] Patent Number: Plant 9,141

[45] Date of Patent: May 16, 1995

[54] GERANIUM PLANT NAMED MERINEON

[75] Inventor: Adrianus W. M. Enthoven, Wateringen, Netherlands

[73] Assignee: Enthoven Breeding B.V., Wateringen, Netherlands

[21] Appl. No.: 197,345

[22] Filed: Feb. 16, 1994

[51] Int. Cl.[6] ..... A01H 5/00

[52] U.S. Cl. ..... Plt./87.12

[58] Field of Search ..... Plt. 87.12

[56] References Cited

U.S. PATENT DOCUMENTS

P.P. 7,908 7/1992 Klemm ..... Plt./87.12

*Primary Examiner*—James R. Feyrer

*Attorney, Agent, or Firm*—Foley & Lardner

[57] ABSTRACT

A new and distinct cultivar of geranium named Merineon, particularly characterized by the combined features of a compact growth habit staying rather narrow; dark green foliage (upper face 137C) with a light and very weak (RHS 137A) zone in the center of the leaves; leaf margins that are double crenated and wavy; flower stalks that are short, sturdy and grow above the plant, inflorescences that are average in size but with many open flowers; flower buds are elliptic in shape; flowers are carmine red, semi-double and have many petals; and flowering time is early to average.

3 Drawing Sheets

The present invention comprises a new and distinct cultivar of geranium, botanically known as *Pelargonium zonale,* and hereinafter referred to by the cultivar name Merineon.

Merineon is a product of a planned breeding program which had the objective of creating new geranium cultivars with semi-double flower form, compact growth habit, fast rooting, good tolerance to Botrytis, superior weather resistance and little need for growth regulators.

Merineon was originated from a hybridization made by the inventor in a controlled breeding program in Wateringen, The Netherlands in 1987. The female parent was an unnamed and proprietary Enthoven seedling, characterized by its compact growth. The male parent of Merineon was an unnamed and proprietary Enthoven seedling, characterized by its weather resistance.

Merineon was discovered and selected as one fowering plant within the progeny of the stated cross by Adrianus W. M. Enthoven in June 1988 in a controlled environment in Wateringen, The Netherlands.

The first act of asexual reproduction of Merineon was accomplished when vegetative cuttings were taken from the initial selection in August 1988 in a controlled environment in Wateringen, The Netherlands under the supervision of Adrianus W. M. Enthoven.

Horticultural examination of selected units initiated in the spring and summer of 1989, and continuing thereafter, have demonstrated that the combination of characteristics as herein disclosed for Merineon are firmly fixed and are retained through successive generations of asexual reproduction.

Merineon has not been observed under all possible environmental conditions. The phenotype may vary with variations in environment such as temperature, light intensity and day length, without, however, any variation in genotype.

The following measurements, and comparisons describe plants grown in Wateringen, The Netherlands under greenhouse and outdoor conditions which approximate those generally used in commercial practice.

The following traits have been repeatedly observed and are determined to be basic characteristics of Merineon, which in combination distinguish this geranium as a new and distinct cultivar:

1. The plant has a compact growth habit and stays rather narrow.
2. The foliage is dark green (upper surfaces RHS 137C) and therefore the plants transport well.
3. The leaves have a light and very weak (RHS 137A) zone in the middle and the leaf margins are doube-crenated and wavy.
4. The leaf stalk is short and sturdy.
5. The flower stalk is sturdy and short and grows above the plant.
6. The inflorescence is of average size with many open flowers.
7. The little flower stalks are long.
8. The flowers are large in diameter.
9. The flower buds are large in diameter.
10. The flowers are carmine red, semi-double and have many petals.
11. The flowering time is early to average.
12. Due to the compact growth habit the plants do not need any growth regulators during the cultivation period.
13. The strong contrast between the color of the foliage and the flowers gives the plant a special lucidity.

Of the many commercial cultivars known to the present inventor, there is no similar comparable variety of Merineon, because of the unique neon flower color.

The accompanying color photographic drawings show typical flower and foliage characteristics of Merineon with colors being as true as possible with illustrations of this type.

Sheet 1 is a side view of Merineon grown in a 10.5 cm pot for approximately 8 weeks showing the foliage, flower stalks and inflorescences.

Sheet 2 is a close-up view of the upper and lower sides of a typical leaf from Merineon.

Sheet 3 is a close-up view of a typical flower from Merineon showing the flowers from the top and bottom.

In the following description color references are made to The Royal Horticultural Society Colour Chart (RHS) and Horticultural Colour Chart (HCC). The color values were determined between 2:10 and 2:30 p.m. on Jul. 31, 1989 under 21,500 Klux light intensity in Wateringen, The Netherlands.

Classification:

*Botanical.*—A hybird of the genus *Pelargonium zonale* cv. Merineon.

*Commercial.*—Zonal geranium.

INFLORESCENCE

A. Umbel:

*Average diameter.*—Indoor: 112 mm.

*Average depth.*—Indoor: 89 mm.

*Peduncle length.*—Indoor: 130 mm.

*Pedicel length.*—Indoor: 37 mm.

*Pedicel color.*—Reddish to dark red at the top.

B. Corolla:

*Average diameter.*—Indoor: 46 mm.

*Form.*—Semi-double (7 to 9 petals).

*Color (general tonality of a distance of three meters)-.*—RHS 57C, HCC 23/1.

*Color (main body, upper surface).*—RHS 50A, HCC 721/3.

*Color (near margin upper face).*—RHS 50A, HCC 721/3.

*Color (lower side of petal).*—RHS 57C, HCC 23/1 at top and RHS 50B near bottom.

*Color (lower side veins).*—RHS 50A.

*Diameter lower petals.*—18 mm.

*Length lower petals.*—26 mm.

*Diameter upper petals.*—15 mm.

*Length upper petals.*—28 mm.

*Petal shape.*—Obovate.

*Sepal color.*—Dark red with green tips.

C. Bud:

*Shape.*—Elliptic.

*Color.*—Slightly lighter than corolla.

*Pedical.*—Red.

D. Reproductive organs:

*Androecium.*—7–9 anthers.

*Gynoecium.*—4–5 stigma.

E. Spring flowering:

*Response period.*—In Wateringen, The Netherlands in 1989, 60% of plants with at least 1 open flower 13 weeks after planting of unrooted cuttings.

F. Outdoor flower production: The flower count in 1989 in Wateringen, The Netherlands was between 46–51 flowers per plant from June through October observation period.

G. Durability: 100% shatter resistance.

PLANT

A. Foliage:

*Form.*—Kidney-shaped, with open base.

*Margin.*—Bicrenate.

*Color.*—Green (RHS 137C).

*Zonation.*—Very Weak (RHS 137C).

*Length.*—41 mm.

*Diameter.*—69 mm.

B. General appearance and form:

*Internode length.*—25 mm.

*Branching pattern.*—An average of 5.7 branches per plant.

*Height.*—257 mm.

*Diameter.*—257 mm.

C. Tolerance of Botrytis: Good.

I claim.

1. A new and distinct cultivar of geranium plant named Merineon, as illustrated and described.

* * * * *

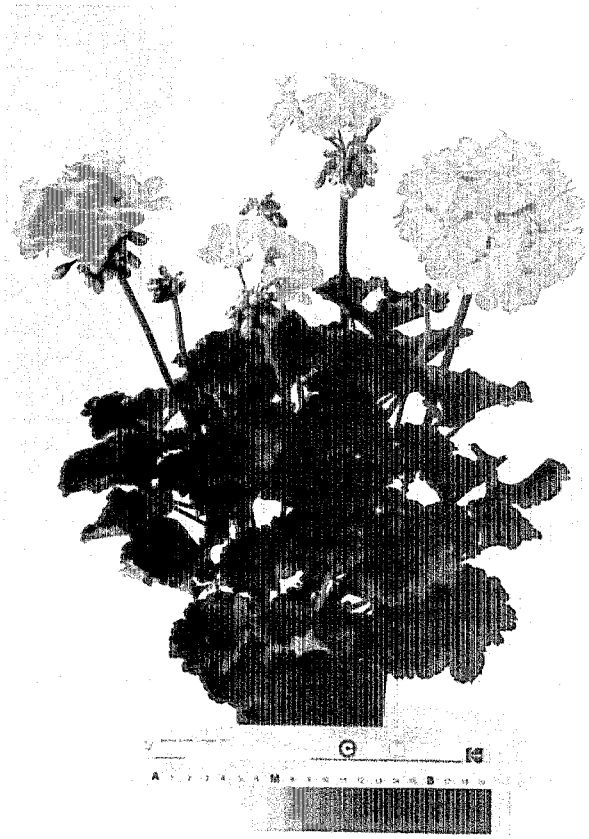

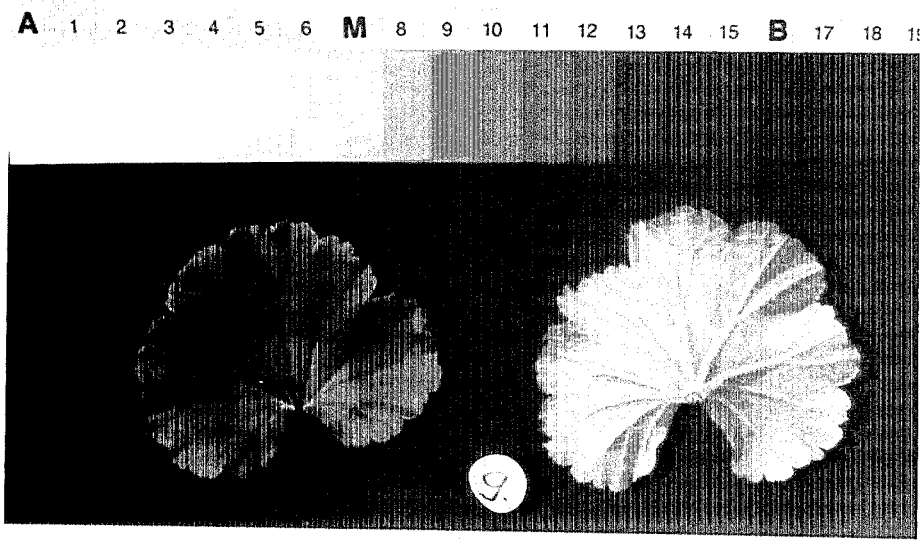
A 1 2 3 4 5 6 M 8 9 10 11 12 13 14 15 B 17 18 19

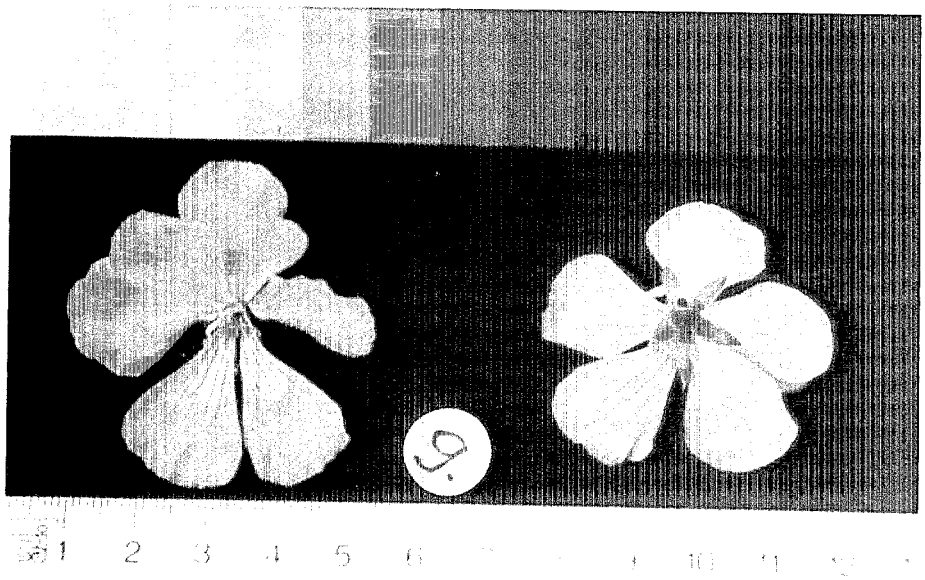
9
1 2 3 4 5 6 10 11